United States Patent [19]

Straub

[11] 4,049,794
[45] Sept. 20, 1977

[54] TREATMENT OF INFECTIONS IN ANIMALS

[75] Inventor: Otto-Christian Straub, Tuebingen, Germany

[73] Assignee: Bayer Aktiengesellschaft, Leverkusen, Germany

[21] Appl. No.: 664,070

[22] Filed: Mar. 5, 1976

Related U.S. Application Data

[62] Division of Ser. No. 482,619, June 24, 1974, which is a division of Ser. No. 313,245, Dec. 8, 1972, abandoned.

[51] Int. Cl.$^2$ .................. A61K 31/00; A61K 45/02; A61K 39/28
[52] U.S. Cl. .................................... 424/167; 424/85; 424/89
[58] Field of Search ................................. 424/89, 167

[56] References Cited

U.S. PATENT DOCUMENTS 3,674,864  7/1972  Angelucci .................. 424/90

Primary Examiner—Sam Rosen
Attorney, Agent, or Firm—Depaoli & O'Brien

[57] ABSTRACT

There is disclosed novel non-antigenic attenuated viruses which non-specifically stimulate the natural defense mechanism of a host organism with a detectable non-specific induction of interferon; to methods for their production and to their use for the prophylaxis and treatment of viral and bacterial infections in human and veterinary medicine. The aforesaid term "non-antigenic attenuated virus" in this application means "an attenuated virus being incapable to cause an immunological cross-reaction with the original virus".

5 Claims, 4 Drawing Figures

TREATMENT OF INFECTIONS IN ANIMALS

BACKGROUND OF THE INVENTION

It has, heretofore, been previously known that the natural, primary defense mechanisms against viral infection are mainly brought into play by the production of interferon although other hitherto unknown factors also play a role and, therefore, cannot be excluded.

Interferon is a protein macro-molecule formed by the action of a virus and a host cell.

Interferon was discovered by A. Isaacs and J. Lindemann, Proc. Roy. Soc. B 147, 258 (1957) while studying virus interference. By producing interferon one virus can interfere with the growth of another virus added subsequently. The viruses need not be related and interference can be induced by inactivated as well as by live virus [G. Bodo, Naturwissenschaften 58 (1971) 425–429; J. L. Le Clero and J. Cogniaus--Le Clerc, Acta Virol. 9 (1965) 18–24; S. Hermodsson, Acta path. Microbiol Scand. 62 (1964) 224–238; M. Harris, Science 170 (1970) 1068–1070)].

Interferons are generally believed to be proteins which cause a non-specific and non-immunological defense reaction against viral infections. Thus, for example, if a virus enters a host organism, the cells of the Reticulo-Endothial (R. E.) System, which constitute the major line of defense in the animal body, within a short time produce large quantities of interferon and produce a high interferon level in the circulatory system. This "circulating interferon" is rapidly distributed throughout the host organism and prevents the further spread of viral infection or of secondary infection. As pointed out above, it has been established that the formation of interferon in a host organism can be stimulated by the therapeutic administration of both active and inactive viruses, however, a serious disadvantage of the therapeutic administration of such viruses is the simultaneous induction of virusspecific antibodies in the host organism which makes more difficult or prevents repeated administration of such viruses for stimulating the non-specific defense mechanisms because of the danger of allergization and/or anaphylatic shock within certain time intervals.

Additionally, there are many quite different microorganisms and substances which can cause formation of interferon by the host organism. Such microorganisms may be bacteria, endotoxins, phyto-haemaglutinins, natural and synthetic ribonucleic acids, such as, for example, polyinosinpolycytidylic acid (Poly I:C) as well as certain systhetic polymers possessing anionic character, for example, polyvinyl sulphate, polyacrylic acid and polymethacrylic acid as well as pyrane copolymers [Y.K.S. Murthy and H. P. Anders, Angew. Chem. internat. Edit. 9 (1970) 480–488]. However, these substances all suffer a serious disadvantage in that they are too toxic, for example, they cannot be physiologically degraded (as synthetic polymers) or that they show other strong side effects (as Poly I:C), so that they cannot be used clinically [Y.K.S. Murthy and H. P. Anders, Angew. Chem. internat. Edit. 9 (1970) 480–488; Nature 223 (1969) 715–718].

THE INVENTION

It has now been discovered that novel, non-antigenic virus can readily be produced which non-specifically stimulates the novel defense mechanisms of a host organisms with a detachable non-specific induction of interferon. The aforesaid term "non-antigenic " here and in the following means "incapable to cause an immunological cross-reaction with the original virus". The invention is of great value in that viral strains attentuated, in accordance with the invention, upon elimination to a host organism neither causes the clinical symptoms characteristic of the virus nor reacts with an immune reply by formation of specific, detachable antibodies towards the original virus. The non-specific stimulation of the defense mechanism (in the host organism), for example, in the form of an interferon induction, on the other hand remains maintained. Furthermore, viruses attentuated in accordance with the invention are well tolerated and do not show the symptoms of toxicity mentioned in connection with the variety of microorganisms and substances mentioned above.

In accordance with the invention, a method is now provided for the production of an attentuated virus that stimulates the natural defense mechanism of a host organism without simultaneously having an antigenic effect, in which method a viral strain is passed through a plurality of tissue-cultures until no virus specific immune reply towards the original virus, but only a non-specific induction of interferon, in a host organism, can still be detected.

The invention further provides, as a new material, an attentuated viral strain that stimulates natural defense mechanism of a host organism with a detectable non-specfic induction of interferon without at the same time having an antigenic effect.

As used herein, the expression "a virus of the invention" contemplates an attenuated viral strain as defined in the preceding paragraph whether or not produced by the method of the invention.

The tissue-culture passages may be carried out in any desired manner, and the method chosen will depend upon the particular virus used.

However, it is preferred to use the method described in German Offenlegungsschrift No. 2033946. This Offenlegungsschrift describes a method for producing an IPV vaccine [IPV = infectious pustular vulvovaginitis = *Exanthema coitale vesiculosum bovis* = cattle blister rash] comprising growing an electrophoretically homogeneous virus population obtained from vesicular exanthema of IPV by passages on tissue cultures of cattle cells at 36°–40° C. for 12–100 hours, and separating the product by centrifugation. In this case preferred tissue for the tissue culture is kidney, suprarenal or testicular tissue of calves. For further details of this method of reader is referred to Offenlegungsschrift No. 2,033,946.

Surprisingly, the virus of the invention, over sufficient further passages, no longer exhibits the frequently observed immunological cross-reaction with the original virus, but retains only the desired non-specific induction of interferon. As a result, the clinical symptoms which arise on application of insufficiently attentuated virus strains are avoided. The method of the invention thus represents valuable enrichment of pharmacy.

The virus of the invention can be used for the prophylaxis and treatment of viral infections both in human medicine and in veterinary medicine. In particular, the viruses of the invention are suitable for the prophylaxis and treatment of influenzal symptoms in man and of infections of the respiratory tract of animals.

The present invention further contemplates pharmaceutical compositions containing, as an active ingredient, a virus of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as an active ingredient a virus of the invention in the form of a sterile isotonic or buffered aqueous solution.

A further embodiment of the invention provides a medicment, in dosage unit form, comprising a virus of the invention either alone or in admixture with a diluent.

The invention also provides a medicament in the form of tablets (including lozenges and granules), dragees, capsules, pills, ampoules or suppositories comprising a virus of the invention either alone or in admixture with the diluent.

"Medicament" as used herein means physically discrete coherent portions suitable for medical administration. "Medicament in dosage unit forms" as used herein means physically discrete coherent portions suitable for medical administration each containing a single dose or a multiple (up to four times) or sub-multiple (down to a fortieth) of a single dose of the virus of the invention.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granules or powders.

The diluents to be used in pharmaceutical compositions (e.g. granulates) adapted to be formed into tablets, dragees, capsules and pills include the following:

a. fillers and extenders, e.g., starch, sugars, mannitol and silicic acid;

b. binding agents, e.g., carboxymethyl cellulose and other cellulose derivatives, alginates, gelatin, and polyvinyl pyrrolidone;

c. moisturizing agents, e.g., glycerol;

d. disintegrating agents, e.g., agar-agar, calcium carbonate and sodium bicarbonate;

e. agents for retarding dissolution, e.g. paraffin;

f. resorption accelerators, e.g., quaternary ammonium compounds;

g. surface active agents, e.g. cetyl alcohol, glycerol monostearate;

h. adsorptive carriers, e.g., kaolin and bentonite;

i. lubricants, e.g., talc, calcium, and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents contemplated for use in the pharmaceutical compositions of the invention adapted to be formed into suppositories can, for example, be the usual water-soluable or water-insoluable diluents, such as polyethylene glycols and fats [e.g., cocoa oil and high esters (e.g., $C_{14}$-alcohol with $C_{16}$-fatty acid)] or mixtures of these diluents.

The pharmaceutical compositions of the invention which are in the form of ointments, pastes, creams and gels can, for example, contain the usual diluents, e.g., animal and vegetables fats, waxes, paraffins, starch, tragacanth, cellulose derivatives, polyethylene glycols, silicones, bentonites, silicic acid, talc and zinc oxide or mixtures of these substances.

The pharmaceutical compositions of the invention which are in the form of powders and sprays can, for example, contain the usual diluents, e.g., lactose, talc, silicic acid, aluminum hydroxide, calcium silicate, and polyamide powder or mixtures of these substances. Aerosol sprays can, for example, contain the usual propellants, e.g., chlorofluorohydrocarbons.

The pharmaceutical compositions of the invention which are in the form of solutions and emulsions can, for example contain the customary diluents (with, of course, the aforementioned exclusion of solvents having a molecular weight below 200 except in the presence of a surface-active agent), such as solvents, dissolving agents and emulsifiers, specific examples of such diluents being water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic and/or buffered.

The pharmaceutical compositions of the invention which are in the form of suspensions can contain the usual diluents, such as liquid diluents, e.g., water, ethyl alcohol, propylene glycol, surface-active agents (e.g., ethoxylated isostearyl alcohols, polyoxyethylene sorbite and sorbitane esters), microcrystalline cellulose, aluminum metahydroxide, bentonite, agar-agar and tragacanth or mixtures thereof.

All the pharmaceutical compositions according to the invention can also contain coloring agents and preservatives as well as perfumes and flavoring additions (e.g., peppermint oil and eucalyptus oil) and sweetening agents (e.g., saccharin).

Finally, the pharmaceutical compositions of the invention may contain stabilizers. As examples of possible stabilizers there may be listed amino acids, sugars, proteins, polysaccharides and polyalkylene glycols, especially polyethylene glycol. The stabilizers can be added, either in aqueous solution or in the lyophilized state.

In addition, the virus of the invention, the pharmaceutical compositions and medicaments according to the invention can also contain other viral strains, or pharmaceutically active compounds.

Any diluent in the medicaments of the present invention may be any of those mentioned above in relation to the pharmaceutical compositions of the present invention. Such medicaments may include solvents and molecular weight less than 200 as sole diluent, such as water.

The discrete coherent portions constituting the medicament according to the invention (whether in dosage unit form or not) may be, for example, any of the following: tablets (including lozenges and granules), pills, dragees, capsules, suppositories, and ampoules. Some of these forms may be made up for delayed release of the active ingredient. Some, such as capsules, include a protective envelope which renders the portions of the medicament physically discrete and coherent.

The preferred dosage rates for administration of the medicaments of the invention are discussed below:

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g., tablets).

The present invention further provides a method of combating (including prevention, relief and cure of) viral infections in human and non-human animals, which comprises administering to the animals a virus of the invention either alive or inactivated, and alone or in admixture with a diluent or in the form of a medicament according to the invention.

Vaccines comprising the virus of the invention can be administered in conventional ways. Primarily, however, they will be administered orally, parenterally (for example, intramuscularly and subcutaneously), or locally. They are preferably applied to the mucuous membranes of the subject, for example, as sprays. Preferred pharmaceutical compositions and medicaments are, therefore, those adapted for oral, intramuscular, subcutaneous, and local administration.

In the human medical field, a solution which contains $10^4$ to $10^8$, preferably $10^6$ to $10^7$ $CiD_{50}$ (Culture-infections Dose) units per ml. is preferably employed as a vaccine in amounts of 0.1 to 5 ml., preferably 0.5 to 2 ml., for intramuscular application, and in amounts of 0.5 to 5 ml., preferably 1 to 2 ml., when formulated as a spray.

When using vaccines containing the virus of the invention in veterinary medicine, the dosage range depends on the species of animal to be vaccinated, and the type of application.

Some examples are given below. In connection with those it should be noted that the particular vaccine used in each case in general contained $10^4$ to $10^8 CiD_{50}$ units per ml., perferably $10^6$ to $10^7$ $CiD_{50}$ units per ml.

Thus, on intramuscular application in cattle it has proved appropriate to employ 0.5 to 10 ml., preferably 1 to 5 ml., of vaccine of the above-mentioned concentration. When formulated as a spray, 1 to 15, preferably 2 to 6 ml. are employed.

In pigs it has proved appropriate, in intramuscular application, to apply 0.5 to 10 ml., preferably 1.5 to 5 ml., of a vaccine of the above-mentioned concentration. When the vaccine is applied as a spray, 1.5 to 10 ml., preferably 2 to 5 ml., are employed in the case of pigs.

EXAMPLE 1

A strain of IPV virus was obtained according to Offenlegungsschrift No. 2,033,946 as follows:

The natural strain of the vesicular exanthema virus was taken directly from an infected animal, purified and tested electrophoretically for homogenity of the virus population, and grown on calf kidney cell cultures in Earle medium with an addition of lactabumin at 37°–39° C. After appearance of the cytopathogenic effect (about 24 to 48 hours) which is indicated by 80–100% disintegration of the cell cultures, the supernatant was decanted off and centrifuged at 4°C. for 40 minutes to 2000 g. The sediment was rejected, and the clear supernatant solution taken for further treatment.

In all, 200 passages through tissue cultures as described above produced an attenuated viral strain according to Offenlegungsschrift No. 2,033,946.

The resulting IPV inoculation strain was subjected to 150 further passages through tissue culture as described above. Thus, an attenuated IPV viral strain having the properties disclosed herein was obtained as an aqueous solution.

After application of this solution to the mucuous membranes of the respiratory and genital tract, no clinical symptoms occurred in the animals. With none of the generally customary methods was it possible to detect antibodies *reacting with the original virus in the serum after the customary time of 4 weeks after inoculation. However, the formation of interferon ** was detachable, which resulted in the animals being protected against infection with virulent virus.

*Antibodies can be detected by customary methods, such as serum neutralization test, double diffusion method, or immunoelectrophoresis.
**Interferon can be detected by customary methods such as the plaque reduction method, reduction of the virus haemagglutinin titer or quantitative haemadsorption method.

EXAMPLE 2

In four herds — one insemination station and three raising establishments — animals suffered partly from cough and partly fron non-specific genital infections, demonstrably of non-viral origin. After inoculation with the interferon-inducing virus strain described in Example 1, the infected animals were completely healed within a few weeks. On the other hand, there was no humoral immune response towards the original virus.

EXAMPLE 3

The AUJESZKY/pseudo-rabies virus strain S/T, attenuated by 300 passages through tissue cultures, was inoculated partly intra-nasally and partly intramuscularly in pigs suffering from non-specific diseases of the respiratory tract, resembling piglet influenza. After 3 weeks, the illness symptoms had disappeared in the treated pigs — but not in control animals — and the specific immune reply had not manifested itself.

EXAMPLE 4

Influenza virus A 1—strain FM 1 was adapted on primary monkey kidney cell cultures and passed through 350 tissue culture passages.

Twenty test persons, aged between 30 and 40 years, of which the serum antibody titers against A 1—FM 1 were <1:32, were each vaccinated with virus solutions attentuated in this way, using 500 CCA (Chicken Cell Agglutinating) units per ml. The solutions were applied subcutaneously in 10 persons and intra-nasally in 10 persons.

Four days after the vaccination, the treated persons and 10 controls of the same age group having antibody titers <1:32 were experimentally challenged by intra-nasal spraying of 500 CCA units per ml. of a pathogenic A 1—FM 1 virus solution.

The inoculated persons were protected against infection while nine out of the 10 controls showed influenzal symptoms.

Figure 3:
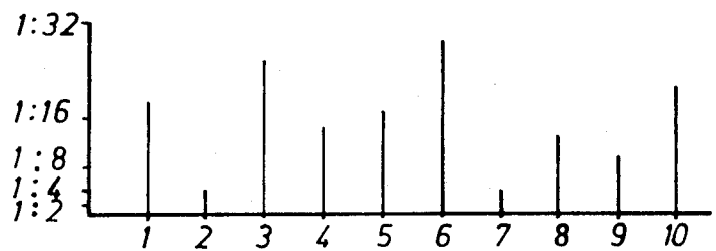

FIG. 3 shows the serum antibody titer of the 10 control persons before the exposure to active virus.

Figure 4:
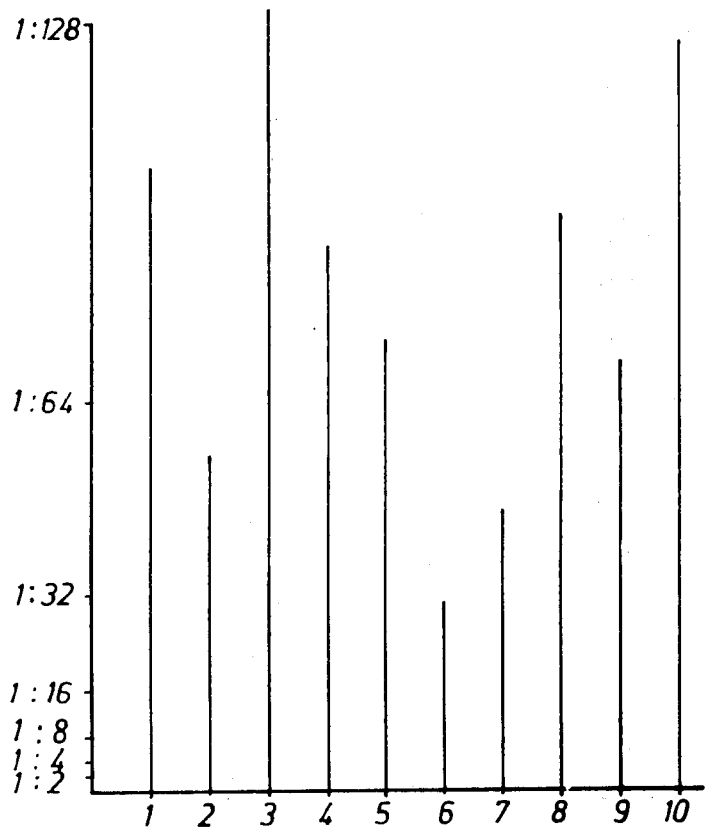

FIG. 4 shows the serum antibody titer 14 days after the exposure to active virus. Only in control person No. 6 were no influenza symptoms detectable.

Figure 1:
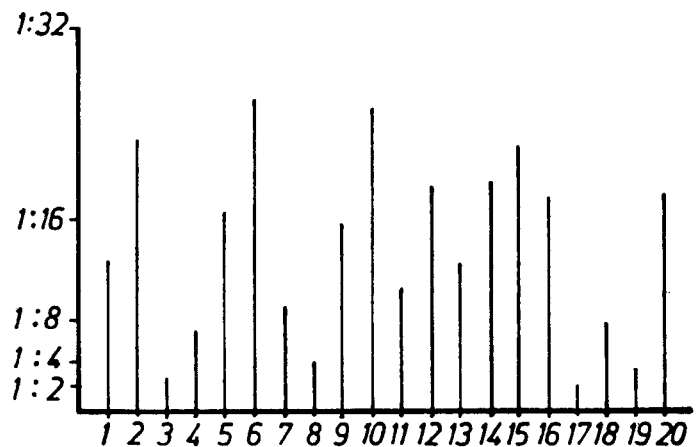
FIG. 1 shows the level of the serum antibody titer (ordinate) in the twenty different test persons, before vaccination.
Figure 2:
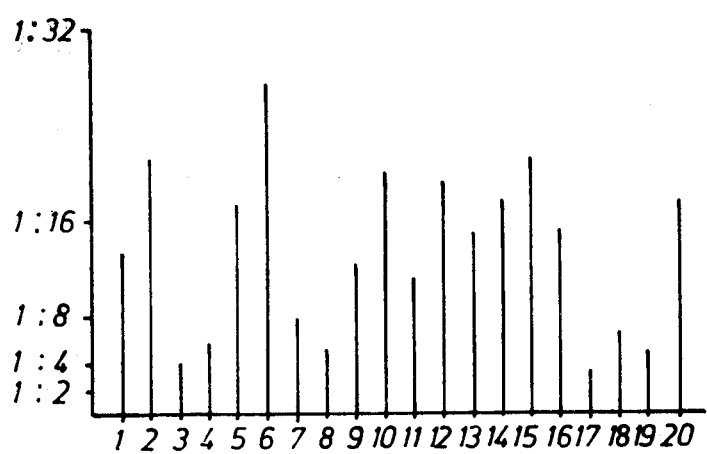
FIG. 2 shows the same titer 14 days after the active virus treatment.

No rise in the virus-specific antibody titer was detectable in the sera of the vaccinated persons (FIG. 2). The antibody titer against A 1—FM 1 in the convalescent sera of the controls were between 1:32 and 1:28 (FIG. 4).

While the invention has been described in the specific and illustrated in Examples 1 and 2 with respect to IPV virus, it should be immediately apparent that the invention is not limited to such virus as may be observed from illustrative Examples 3 and 4. Accordingly, it is intended that the invention, as defined in the appended claims, be interpreted insofar as the state of the art permits.

What is claimed is:

1. A method for prophylaxis and treatment of respiratory and genital infections in animals which comprises administering to the animals an attenuated virus capable of stimulating the natural defense mechanism of a host animal with a detectable non-specific induction of interferon without antigenic effect, wherein said attenuated virus is produced by passing a virus through a plurality of at least 300 tissue cultures to achieve a degree of attenuation such that antigenic effect cannot be detected in the presence of a detectable non-specific induction of interferon in said host animal, and wherein said virus is AUJESZKY/psuedo-rabies virus, AUJESZKY/ psuedo-rabies virus—strain S/T, Influenza virus Al, Influenza virus Al—strain FM1 or IPV virus.

2. The method of claim 1 in which the animals are cattle.

3. The method of claim 1 in which the animals are pigs.

4. The method of claim 1 in which the virus is applied as a spray to a mucuous membrane of the animal.

5. The method of claim 1 in which the virus is applied to the animal intramuscularly.